United States Patent [19]

Barlow et al.

[11] Patent Number: 4,581,471

[45] Date of Patent: Apr. 8, 1986

[54] PROCESS FOR THE PRODUCTION OF UNSATURATED CARBOXYLIC ACIDS AND/OR ESTERS

[75] Inventors: Michael T. Barlow, Byfleet; David G. Stewart, Epson, both of England

[73] Assignee: The British Petroleum Company P.L.C., London, England

[21] Appl. No.: 598,464

[22] Filed: Apr. 9, 1984

[30] Foreign Application Priority Data

Apr. 12, 1983 [GB] United Kingdom ............... 8309837
May 18, 1983 [GB] United Kingdom ............... 8313713
May 25, 1983 [GB] United Kingdom ............... 8314475

[51] Int. Cl.[4] ................. C07C 67/343; C07C 51/353
[52] U.S. Cl. ................................. 560/210; 560/104; 560/190; 562/599; 260/410.9 R
[58] Field of Search ............. 560/210, 211, 104, 190; 562/599; 260/410.9 R

[56] References Cited

U.S. PATENT DOCUMENTS

| | | | |
|---|---|---|---|
| 2,734,074 | 2/1956 | Redmon | 560/210 |
| 3,014,958 | 12/1961 | Koch et al. | 560/210 |
| 3,089,902 | 5/1963 | Vitcha et al. | 560/210 |
| 3,499,028 | 4/1970 | McTeer | 560/210 |
| 3,654,345 | 4/1972 | Jentsch | 560/210 |
| 4,336,403 | 6/1982 | Merger et al. | 560/211 |
| 4,452,907 | 6/1984 | Bell et al. | 502/60 |

OTHER PUBLICATIONS

Hackh's Chemical Dictionary, 4th Ed. (1969), at p. 173.

Primary Examiner—Natalie Trousof
Assistant Examiner—L. Hendriksen
Attorney, Agent, or Firm—Brooks Haidt Haffner & Delahunty

[57] ABSTRACT

Unsaturated carboxylic acids and/or esters thereof are produced by reacting an aldehyde comprising formaldehyde or acetaldehyde with either a saturated carboxylic acid ester or anhydride in the vapor phase in the presence as catalyst of a high silica crystalline aluminosilicate zeolite in which the cation is $H^+$ and/or a transition metal and/or a rare earth metal. In a modification of the process instead of formaldehyde there is used methanol/molecular oxygen and in the catalyst there is included either an oxidative or an oxidative/dehydrogenative component.

16 Claims, No Drawings

PROCESS FOR THE PRODUCTION OF UNSATURATED CARBOXYLIC ACIDS AND/OR ESTERS

The present invention relates to a process for the production of unsaturated carboxylic acids and/or esters by reacting either formaldehyde or acetaldehyde with a saturated carboxylic acid derivative at elevated temperature in the vapour phase in the presence of a catalyst.

U.S. Pat. No. 3,701,798 describes a process for the preparation of alpha, beta-unsaturated compounds having the generic formula $$CH_2{:}C(R)(X) \text{ or } CH_2{:}C(X)R^1C(X){:}CH_2$$

wherein R, $R_1$ and X are as defined below, which comprises passing a mixture of formaldehyde and a compound having the generic formula $RCH_2X$ or $$XCH_2R_1CH_2X$$

in which R is hydrogen, or a saturated aliphatic hydrocarbon radical having 1 to 20 carbon atoms, $R_1$ is a carbon-carbon bond or a divalent saturated aliphatic hydrocarbon radical having 1 to 20 carbon atoms and X is a functional group having the formula $$-CHO, -CR^{11}O \text{ or } -CN$$

wherein $R^{11}$ is a lower alkyl radical at a temperature of 300° to 525° C. over a catalyst consisting essentially of one or more inorganic oxides of rare earth metals of the lanthanide series impregnated on a silica gel, alumina or kieselguhr support.

U.S. Pat. No. 4,324,908 describes a process for producing unsaturated carboxylic acids and esters which comprises passing into a reaction zone, a vaporous mixture of a saturated monocarboxylic acid or its ester with formaldehyde or a formaldehyde derivative, at a temperature of from 200° C. to about 450° C. in the presence of a catalyst having the empirical formula $$A_aPO_x$$

wherein
A is Fe, Ni, Co, Mn, Cu, Ag or mixtures thereof;
a is 0.2-3.0; and
x is determined by the nature and oxidation state of the other elements.

It is further disclosed in U.S. Pat. No. 4,324,908 that the catalysts may be used unsupported, but the use of a suitable carrier, such as silica, alumina, mixtures of silica and alumina, amorphous silica-alumina, crystalline aluminosilicates, titania, natural clays and such is preferred. In the background of the invention it is disclosed that X or Y zeolites with cesium, rubidium or potassium cations as found in U.S. Pat. No. 4,115,424 are examples of other catalysts which have been found useful in this reaction. In point of fact however, U.S. Pat. No. 4,115,424 relates to a catalyst comprising a crystalline aluminosilicate of faujasite structure with $SiO_2/Al_2O_3$ mole ratio in the range of about 2 to about 8 and including potassium, rubidium or cesium cations or combinations thereof, and containing boron or phosphorus or combinations thereof and their use in the alkylation of toluene to styrene and ethylbenzene, not the production of unsaturated carboxylic acids and esters.

We have now found that high silica synthetic crystalline aluminosilicates catalyse the reaction of either formaldehyde or acetaldehyde with a saturated carboxylic acid ester or anhydride to produce unsaturated carboxylic acids and/or esters. High silica crystalline aluminosilicates, that is crystalline aluminosilicates having a silica to alumina molar ratio greater than 10:1, are to be distinguished from X and Y-type zeolites as used in the process of U.S. Pat. No. 4,115,424 not only in that they have a higher silica to alumina molar ratio but also in that they are more acidic and have higher mechanical and thermal stabilities.

Accordingly, the present invention provides a process for the production of an unsaturated carboxylic acid and/or an ester thereof by reacting an aldehyde comprising formaldehyde or acetaldehyde with a saturated carboxylic acid derivative in the presence of a catalyst at elevated temperature and in the vapour phase characterised in that the saturated carboxylic acid derivative is either an ester or an anhydride and the catalyst comprises a synthetic crystalline aluminosilicate having the composition in terms of mole ratios of oxides:

$$0.9 \pm 0.2 \, M_{2/n}O{:}Al_2O_3{:}YSiO_2{:}zH_2O$$

wherein
M is $H^+$ and/or a transition metal and/or a rare earth metal cation having a valence n,
Y is an integer greater than 10, and
z is an integer in the range from 0 to 40.

The aldehyde reactant is either formaldehyde or acetaldehyde, preferably formaldehyde. Formaldehyde may be derived from any commercial source of formaldehyde such as aqueous, alcoholic, or polymeric formaldehyde. Suitable sources of formaldehyde include formalin, methylal and trioxane. Similarly acetaldehyde may be derived from any commercial source of acetaldehyde.

The saturated carboxylic acid ester suitably has the formula:

$$R^1CH_2X \text{ or } XCH_2R^2CH_2X$$

in which $R^1$ is hydrogen, phenyl or an aliphatic hydrocarbon radical, $R^2$ is either a carbon/carbon bond or a divalent aliphatic hydrocarbon radical and X is a functional group having the formula:

$$-COOR^3$$

wherein $R^3$ is a hydrocarbon or substituted hydrocarbon radical. Suitable carboxylic acid esters include methyl acetate, ethyl acetate, propyl acetate, methyl propionate, ethyl butyrate, methyl hexanoate, ethyl heptanoate and dimethyl adipate.

Particularly preferred reactants are formaldehyde and methyl acetate which produce methyl acrylate and/or acrylic acid and acetaldehyde and methyl acetate which produce methylcrotonate.

The saturated carboxylic acid anhydride may suitably be of the formula $R^4CH_2CO.O.COCH_2R^5$ wherein $R^4$ and $R^5$ are independently either hydrogen or alkyl groups. Suitably the alkyl group may be a $C_1$ to $C_6$ alkyl group. Examples of suitable carboxylic acid anhydrides include acetic anhydride, propionic anhydride and the mixed anhydride thereof. The reaction of formaldehyde with acetic anhydride produces a product comprising acrylic acid.

The molar ratio of acid derivative to aldehyde is not critical but is suitably within the range from 1:1 to 25:1. Optimum ratios will however be dependent on the reaction conditions and nature of the reactant and may be readily determined by persons skilled in the art.

As regards the crystalline aluminosilicate having the aforesaid composition, Y is preferably in the range from 15 to 100. A variety of synthetic crystalline aluminosilicates conforming with the aforesaid compositional formula may suitably be employed. An example of a preferred class of crystalline aluminosilicates are those designated as MFI zeolites in the Atlas of Zeolite Structure Types by W. M. Meier and D. H. Olson, published by the Structure Commission of the International Zeolite Association, 1978. These are generally prepared by crystallisation for a time greater than 0.5 hr at a temperature in the range from 80° to 220° C., preferably from 120° to 175° C., from a gel comprising (i) a source of silica ($SiO_2$), (ii) a source of alumina ($Al_2O_3$), (iii) a mineralising agent selected from oxides and salts of alkali and alkaline earth metals ($X_{2/b}O$ wherein b is the valency of X), (v) an organic base (B), as hereinafter defined, and (vi) water and/or alcohol (ROH), in the following molar proportions:

$SiO_2:Al_2O_3$ greater than 12:1, preferably in the range 15:1 to 100:1,
$SiO_2:X_{2/b}O = 1000:1$ to 50:1
$SiO_2:B = 50:1$ to 1:20, and
$SiO_2:H_2O$ or ROH less than 1:10.

The term organic base as used hereinbefore means any organic material for which $-\log_{10}K$ for the reaction:

$$B + H_2O \rightleftharpoons BH^+ + OH^-$$

is less than 7, where $K = [BH^+][OH^-]/[B]$.

Suitable organic bases include:
(i) tetrahydrocarbylammonium salts of the formula:

$$R^1R^2R^3R^4N^+X^-$$

wherein $R^1$, $R^2$, $R^3$ and $R^4$ are independently either aryl, substituted aryl, alkyl, substituted alkyl, cycloalkyl, substituted cycloalkyl or hydrogen and $X^-$ is an organic or an inorganic anion. Preferably $R^1$, $R^2$, $R^3$ and $R^4$ are alkyl groups containing from 1 to 5 carbon atoms. Preferably $X^-$ is a halide or hydroxide ion. Suitable tetraalkylammonium salts include tetraethylammonium hydroxide and tetrapropylammonium hydroxide. Alternatively, the precursors of tetraalkylammonium compounds may be used.

(ii) amines having the formula: either $R^1R^2R^3N$, or $R^1R^2N(CH_2)_xNR^3R^4$ wherein x is an integer in the range 1 to 20, or $R^1R^2N(CH_2)_yN(CH_2)_zNR^3R^4$ wherein y and z are integers in the range 1 to 20.

Suitable amines include $C_1$ to $C_9$ primary monoalkylamines, such as n-ethylamine, n-propylamine and n-butylamine.

(iii) Mono-, di- and tri-alkanolamines such as monoethanolamine, diethanolamine and triethanolamine, or their precursors in the form of an alkylene oxide and ammonia.

Suitable sources of silica include, for example, sodium silicate, silica hydrosol, silica gel, silica sol and silicic acid. The preferred source of silica is an aqueous colloidal dispersion of silica particles. A suitable commercially available source of silica is LUDOX* Colloidal Silica manufactured by DuPont (* Registered Trade Mark).

Suitable sources of alumina include, for example, sodium aluminate, aluminium sulphate and alumina. The preferred source of alumina is sodium aluminate prepared by dissolving particulate alumina in excess sodium hydroxide solution.

The preferred mineralising agents are alkali and alkaline earth metal hydroxides and halides, such as for example, lithium hydroxide, sodium hydroxide, potassium hydroxide, potassium bromide and calcium bromide. The preferred mineralising agent is sodium hydroxide.

It will be appreciated that each source of silica, alumina, alkali or alkaline earth metal can be supplied by one or more initial reactants and then mixed together in any order. For example, sodium silicate is a source of both sodium and silica and an aluminosilcate is a source of both alumina and silica. Thus, the source of alumina and the source of silica may be supplied in whole or in part by an aluminosilicate, which may be either crystalline or amorphous.

Specific MFI-type zeolites and processes for their production utilising organic bases are described in U.S. Pat. Nos. 3,702,886; 3,709,979; 4,205,053; 4,166,099; 4,139,600 and 4,151,189; UK Pat. Nos. 1,365,318 and 1,567,948 and European patent application publication Nos. 2899 and 2900, for example.

Alternatively, the organic base may be replaced by a source of ammonium ions as described in our European patent application publication No. 30811, U.S. Pat. No. 4,199,556 and UK application publication No. 2,018,232A.

Alternatively, other crystalline aluminosilicates such as ferrierite as described in UK Pat. No. 1,436,524, Theta-1 as described in European patent application publication No. 57049, FU-1 as described in U.S. Pat. No. 4,209,498, nu-1 as described in UK Pat. No. 1,559,367, ZSM-5/ZSM-11 as described in U.S. Pat. No. 4,229,424, ZSM-35 as described in U.S. Pat. No. 4,146,584, ZSM-23 and zeolite Beta may be used.

Furthermore, there may also be used dealuminised faujasites.

As prepared the aforementioned crystalline aluminosilicates will almost certainly contain ions other than hydrogen ions and transition metal ions, for example alkali metal and/or alkaline earth metal ions, organic nitrogen ions and ammonium ions and possibly also organic bases deposited in the pores and on the surface thereof. In order to obtain a catalyst having the desired composition, it is necessary to replace the exchangeable cations with hydrogen ions or transition metal ions. This may be accomplished by the use of conventional ion-exchange techniques. Furthermore, it is desirable after exchange and indeed it is necessary before exchange of crystalline aluminosilicates derived from certain organic bases, to calcine the crystalline aluminosilicate. Calcination may be effected by heating, suitably in a stream of air, at a temperature in the range from 400° to 600° C. for at least 0.5 hr.

Suitable transition metal ions include ions of the metals of Group VIII of the Periodic Table according to Mendeleef, for example iron, cobalt and manganese and metals of the lanthanide series, for example praseodymium.

The temperature at which the acid derivative is reacted with the aldehyde may suitably be in the range from 300° to 525° C., preferably from 350° to 500° C., though higher and lower temperatures may be employed if desired. Pressure is not critical but is suitably such as to be consistent with maintaining the reactants in the vapour phase.

The process may be operated batchwise or continuously, preferably continuously. Residence times for continuous operation are preferably short, for example less than 20 seconds.

In a particular modification of the present invention instead of using formaldehyde, there may be fed the precursors of formaldehyde in the form of methanol and an oxygen-containing gas provided that the catalyst also contains either an oxidative or an oxidative/dehydrogenative component. The methanol employed may suitably be a commercially available methanol, though more pure and less pure grades may be employed if so desired. The oxygen-containing gas may suitably be air, though gases richer in oxygen, for example molecular oxygen or molecular oxygen/air mixtures, or poorer in oxygen, for example air/inert gas mixtures may be employed if so desired.

The oxidative or oxidative/dehydrogenative component of the catalyst suitably comprises one or more of the elements copper, silver, molybedenum, tungsten, vanadium, chromium and antimony either alone or in combination with one or more of the elements iron, cobalt, nickel, bismuth, aluminium, phosphorus, titanium, selenium and tellurium. The elements may either be exchanged using conventional techniques with exchangeable cations associated with the synthetic crystalline aluminosilicate or may be impregnated on to the synthetic crystalline aluminosilicate, again using known techniques, or may be both exchanged and impregnated. An example of a suitable catalyst is a crystalline aluminosilicate in which at least some of the $H^+$, transition metal or rare earth metal cations are exchanged with either copper or silver cations. Alternatively, the catalyst may comprise an admixture of the aforesaid synthetic crystalline aluminosilicate and either an oxidation or an oxidation/dehydrogenation catalyst comprising the aforesaid elements, either unsupported or supported on an inert support. Suitable such oxidation or oxidation/dehydrogenation catalysts are described in "Propylene and Its Industrial Derivatives" edited by E. G. Hancock, published by Ernest Benn Limited, London and Tonbridge 1973, (p391), chapter 10 entitled "Catalyst Types of Interest in the Oxidation of Propylene to Acrylic Acid." In a further alternative a synthetic crystalline aluminosilicate in which the cations are $H^+$ and/or a transition metal and/or a rare earth metal cation may be admixed with a synthetic crystalline aluminosilicate exchanged wholly or partly with, for example, copper and/or silver cations.

In this modification the elevated temperature employed may suitably be in the range from 250° to 450° C., preferably from 300° to 400° C.

The invention will now be illustrated by reference to the following Examples. In the Examples reference will be made to X-MFI($NH_3$) zeolite and X-MOR zeolite. X-MFI($NH_3$) zeolite is an MFI-type zeolite crystallised from a gel containing ammonium ions as described in EP-A-30811 and X is a cation, for example H. X-MOR zeolite is a mordenite-type zeolite having a cation X. Both X-MFI($NH_3$) and X-MOR-type zeolites have silica to alumina molar ratios greater than 10:1.

EXAMPLE 1

A sample of the hydrogen form of an MFI($NH_3$) zeolite was charged in the form of pellets into a quartz U-tube reactor. Between 10 and 20 mls of the zeolite was employed. The U-tube reactor was placed in a molten tin bath maintained at a temperature of 390° C. and a feed consisting of a 3:1 molar ratio of methyl acetate to formaldehyde was passed over the zeolite at a contact time of 4 seconds (NTP). Flow of feed across the zeolite was assisted by a slow flow of nitrogen. Products of the reaction were removed from the gas phase using a methanol stripper and yields of product were determined by G.C. Analysis of the effluent from the stripper.

EXAMPLE 2

The procedure of Example 1 was repeated except that the H-MFI($NH_3$) zeolite was replaced by a Pr-MFI($NH_3$) zeolite, the temperature was reduced to 350° C. and the contact time was increased to 8 seconds (NTP).

EXAMPLE 3

The procedure of Example 2 was repeated except that the temperature was increased to 400° C. and the contact time was reduced to 4 seconds (NTP).

EXAMPLE 4

The procedure of Example 2 was repeated except that the temperature was increased to 425° C.

EXAMPLE 5

The procedure of Example 3 was repeated except that the contact time was increased to 8 seconds (NTP).

EXAMPLE 6

The procedure of Example 1 was repeated except that the H-MFI($NH_3$) zeolite was replaced by a V-MFI($NH_3$) zeolite.

EXAMPLE 7

The procedure of Example 1 was repeated except that the H-MFI($NH_3$) zeolite was replaced by a Cr-MFI($NH_3$) zeolite.

EXAMPLE 8

The procedure of Example 1 was repeated except that the H-MFI($NH_3$) zeolite was replaced by a La-MOR zeolite and the temperature was increased to 425° C.

EXAMPLE 9

The procedure of Example 1 was repeated except that the H-MFI($NH_3$) zeolite was replaced by a steamed sample of H-MFI($NH_3$) zeolite.

The results in terms of percent yield (molar) on formaldehyde fed after one hour on stream for Examples 1 to 9 are given in the Table.

EXAMPLE 10

12.5 g of the hydrogen form of zeolite MFI($NH_3$) was placed in a quartz U-tube reactor and heated in a bath of molten tin to 390° C. A mixture of acetic anhydride and formaldehyde (3:2 molar) was passed over the catalyst at a rate of 23 mls per hour. After 1 hour on stream, the reaction products were analysed by capillary G.C. and shown to contain a 6.5% molar yield of acrylic acid based on formaldehyde fed.

EXAMPLE 11

12.5 mls of a molybdenum loaded hydrogen MFI zeolite was mixed with 5 mls of 5% silver loaded on Davison 57 silica. The catalyst was then activated for 18 hours at 500° C. in flowing air.

At the end of this time a 2:1 molar mixture of methyl acetate and methanol were passed over the catalyst, in the vapour phase, together with a stream of dry air at 390° C. After 1 hour a sample of the product stream was analysed and shown to contain methyl acrylate. The molar yield of methyl acrylate based on methanol fed was 7.25%.

EXAMPLE 12

The experimental conditions used were exactly the same as those described in Example 11, except that this time a silver exchanged MFI type zeolite was used as catalyst (12.5 mls). Both methyl acrylate and acrylic acid were detected as products. The molar yield of methyl acrylate, based on methanol fed, after 1 hour on stream was 4.5%.

EXAMPLE 13

Example 12 was repeated, except that in this instance a reaction temperature of 420° C. was used. After 1 hour on stream, the molar yield of methyl acrylate as defined above was 5.7%.

EXAMPLE 14

The procedure of Example 11 was followed, but in this case a chromium exchanged MFI zeolite was used. After 1 hour on stream the molar yield of methyl acrylate was 0.9%.

TABLE

| Example | Catalyst | T(°C.) | Contact Time secs (NTP) | $CH_3CO_2CH_3$ $CH_3CO_2CH_3$:HCHO | % Yield (Molar) on HCHO Fed | |
|---|---|---|---|---|---|---|
| | | | | | $CH_2=CHCO_2CH_3$ | $CH_2=CHCO_2H$ |
| 1 | H—MFI(NH$_3$) | 390 | 4 | 3:1 | 50.7 | 9.0 |
| 2 | Pr—MFI(NH$_3$) | 350 | 8 | 3:1 | 21.2 | —* |
| 3 | Pr—MFI(NH$_3$) | 400 | 4 | 3:1 | 29.3 | —* |
| 4 | Pr—MFI(NH$_3$) | 425 | 8 | 3:1 | 39.2 | —* |
| 5 | Pr—MFI(NH$_3$) | 400 | 8 | 3:1 | 43.9 | —* |
| 6 | V—MFI(MH$_3$) | 390 | 4 | 3:1 | 56.5 | 0.5 |
| 7 | Cr—MFI(NH$_3$) | 390 | 4 | 3:1 | 56.1 | 7.3 |
| 8 | La—MOR | 425 | 4 | 3:1 | 15.7 | 0.3 |
| 9 | H—MFI(NH$_3$) (steamed) | 390 | 4 | 3:1 | 39.3 | 10.5 |

*Not Detected in Test

We claim:

1. A process for the production of an unsaturated carboxylic acid and/or an ester thereof by reacting an aldehyde selected from formaldehyde and acetaldehyde with a saturated carboxylic acid derivative in the presence of a catalyst at elevated temperature and in the vapour phase
   wherein the saturated carboxylic acid derivative is selected from esters and anhydrides
   and the catalyst comprises a synthetic crystalline aluminosilicate having the composition in terms of mole ratios of oxides:

$0.9 \pm 0.2 M_{2/n}O : Al_2O_3 : YSiO_2 : zH_2O$ wherein

M is at least one cation selected from the group consisting of Pr, V, Cr, La, Mo, Mn and H$^+$, said cation having a valence n,
   Y is an integer greater than 10, and
   z is an integer in the range from 0 to 40.

2. A process according to claim 1 wherein the aldehyde is formaldehyde.

3. A process according to claim 1 wherein the acid derivative is a saturated carboxylic acid of the formula:

$R^1CH_2X$ or $XCH_2R^2CH_2X$ in which formula $R^1$ is selected from hydrogen, phenyl and aliphatic hydrocarbon radicals, $R^2$ is either a carbon/carbon bond or a divalent aliphatic hydrocarbon radical and X is a functional group having the formula —COOR$^3$ wherein R$^3$ is a hydrocarbon or substituted hydrocarbon radical.

4. A process according to claim 1 wherein formaldehyde and methyl acetate are reacted to produce methyl acrylate and/or acrylic acid.

5. A process according to claim 1 wherein acetaldehyde and methyl acetate are reacted to produce methyl crotonate.

6. A process according to claim 1 wherein the acid derivative is a saturated carboxylic acid anhydride of the formula $R^4CH_2CO.O.COCH_2R^5$ wherein R$^4$ and R$^5$ are iniependently either hydrogen or alkyl groups.

7. A process according to claim 6 wherein formaldehyde is reacted with acetic anhydride to produce a product comprising acrylic acid.

8. A process according to claim 1 wherein the synthetic crystalline aluminosilicate is an MFI-type zeolite.

9. A process according to claim 1 wherein the cation M is praesodymium.

10. A process according to claim 1, wherein the cation M is vanadium.

11. A process according to claim 1 wherein the cation M is chromium.

12. A process according to claim 1 wherein the cation M is lanthanum.

13. A process according to claim 1 wherein the cation M is molybdenum.

14. A process according to claim 1 wherein the cation M is maganese.

15. A process according to claim 1 wherein the cation M is hydrogen.

16. A process according to claim 1, wherein methyl propionate and formaldehyde are reacted to produce methyl methacrylate.

* * * * *

UNITED STATES PATENT AND TRADEMARK OFFICE
CERTIFICATE OF CORRECTION

PATENT NO. : 4,581,471
DATED : April 8, 1986
INVENTOR(S) : MICHAEL T. BARLOW and DAVID G. STEWART It is certified that error appears in the above-identified patent and that said Letters Patent are hereby corrected as shown below:

Table spanning cols. 7-8, In the heading of the fifth column, delete the formula "$CH_3^: CO_2 CH_3$" at top of column.

Col. 8, line 3, "cation" should read --cations--

Col. 8, line 28, "iniependently" should read --independently--

Signed and Sealed this

Twenty-ninth Day of July 1986

[SEAL]

Attest:

DONALD J. QUIGG

Attesting Officer     Commissioner of Patents and Trademarks